United States Patent
Rye (10) Patent No.: US 11,039,840 B2
(45) Date of Patent: Jun. 22, 2021

(54) IMPLANT DETACHMENT

(71) Applicant: MicroVention, Inc., Aliso Viejo, CA (US)

(72) Inventor: Joseph Rye, Oceanside, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 310 days.

(21) Appl. No.: 16/216,864

(22) Filed: Dec. 11, 2018

(65) Prior Publication Data

US 2019/0175183 A1 Jun. 13, 2019

Related U.S. Application Data (60) Provisional application No. 62/597,371, filed on Dec. 11, 2017.

(51) Int. Cl.
| | |
|---|---|
| *A61B 17/12* | (2006.01) |
| *A61N 1/08* | (2006.01) |
| *A61N 1/36* | (2006.01) |
| *A61B 90/00* | (2016.01) |
| *A61B 17/00* | (2006.01) |

(52) U.S. Cl.
CPC .......... *A61B 17/1214* (2013.01); *A61N 1/08* (2013.01); *A61B 2017/00017* (2013.01); *A61B 2017/00929* (2013.01); *A61B 2017/1209* (2013.01); *A61B 2017/12068* (2013.01); *A61B 2090/0811* (2016.02); *A61B 2090/3966* (2016.02); *A61N 1/3605* (2013.01)

(58) Field of Classification Search
CPC .......... A61B 17/1214; A61B 17/12145; A61B 17/1215; A61B 17/12154; A61B 2017/12068; A61B 2017/1209; A61F 2/011; A61F 2/2427; A61F 2/243; A61F 2/2433; A61F 2/2636; A61F 2/2439; A61F 2/95; A61F 2002/9505; A61F 2002/9511; A61F 2/954; A61F 2/962; A61F 2002/9623; A61F 2/966; A61F 2/9661; A61F 2/9662; A61F 2002/9665; A61F 2/97

See application file for complete search history.

(56) References Cited

U.S. PATENT DOCUMENTS

| | | | | |
|---|---|---|---|---|
| 2005/0043755 A1* | 2/2005 | Wilson | ............. | A61B 17/32056 606/200 |
| 2006/0052815 A1* | 3/2006 | Fitz | .................... | A61B 17/1219 606/200 |
| 2011/0301686 A1* | 12/2011 | Bowman | ............ | A61M 25/0021 623/1.11 |
| 2014/0206958 A1* | 7/2014 | Laramy | .............. | A61B 5/14503 600/309 |
| 2014/0277092 A1* | 9/2014 | Teoh | ................... | A61B 17/1214 606/200 |
| 2014/0277093 A1* | 9/2014 | Guo | ................. | A61B 17/12022 606/200 |
| 2014/0277094 A1* | 9/2014 | Chen | ................ | A61B 17/12022 606/200 |
| 2015/0057700 A1* | 2/2015 | Chen | .................. | A61B 17/1214 606/200 |

(Continued)

*Primary Examiner* — Wade Miles
(74) *Attorney, Agent, or Firm* — Inskeep IP Group, Inc.

(57) ABSTRACT

An implant detachment system is described which utilizes a catheter utilizing an LC or tank circuit with an inductor and capacitor. The catheter electrically interacts with an implant delivered through the catheter to detach the implant.

17 Claims, 5 Drawing Sheets

(56) References Cited

U.S. PATENT DOCUMENTS

| | | | | |
|---|---|---|---|---|
| 2015/0173772 A1* | 6/2015 | Bowman | .......... | A61B 17/12163 |
| | | | | 606/200 |
| 2015/0289879 A1* | 10/2015 | Bowman | .......... | A61B 17/12109 |
| | | | | 606/200 |
| 2016/0081693 A1* | 3/2016 | Lorenzo | ........... | A61B 17/12022 |
| | | | | 606/200 |
| 2016/0345904 A1* | 12/2016 | Bowman | ............ | A61B 17/1214 |
| 2018/0338767 A1* | 11/2018 | Dasnurkar | ....... | A61B 17/12168 |

* cited by examiner

IMPLANT DETACHMENT

RELATED APPLICATIONS

This application claims benefit of U.S. Provisional Application Ser. No. 62/597,371 filed Dec. 11, 2017 entitled Embolic Coil Detachment, which is hereby incorporated by reference herein in its entirety.

BACKGROUND OF THE INVENTION

Implants including embolic coils are often used to occlude a target treatment area to treat a variety of vasculature conditions—including aneurysms, fistulas, arteriovenous malformations, left atrial appendage, fallopian tube occlusion, vessel shutdown. The implants are typically connected to a mechanical pusher and must be detached from the pusher to deploy within the vasculature at the target treatment site. The detachment mechanism can be difficult to design, especially as the implants are sized smaller to accommodate smaller blood vessels and smaller treatment sites—such as the neurovasculature. There is a need for an implant detachment system that ensures consistent detachment and that can be sized to accommodate a variety of implant sizes.

SUMMARY OF THE INVENTION

In one embodiment, an implant detachment system comprises a resonant circuit including a capacitor and an inductor. The resonant circuit is used to induce current in a heater coil element of an implant, such as an embolic coil that passes the resonant circuit to detach the embolic coil. In one embodiment, the resonant circuit includes an inductor coil and a capacitor comprising a pair of tubular bands. In one embodiment, the pair of tubular bands are marker bands.

In one embodiment, a powered catheter used in an implant detachment system is described. The powered catheter utilizes a coil and a tubular band to create a resonant circuit. In one embodiment, the resonant circuit is used to induce current in a detachment element of an implant that passes the resonant circuit to detach the implant. In one embodiment, the resonant circuit is used to induce current in a heater coil element of an embolic coil that passes the resonant circuit to detach the embolic coil.

In one embodiment, an embolic coil is described. In one embodiment, the embolic coil includes a plurality of embolic coil segments and at least one heater coil segment separating the plurality of embolic coil segments. In another embodiment, the embolic coil includes an embolic coil segment and a heater coil segment linking the embolic coil segment and a pusher. The heater coil includes a mechanical linkage, such as a tether, which melts or severs in response to heating of the coil.

In one embodiment, a resonant circuit including a capacitor and an inductor used in an implant detachment system is described. In one embodiment, the resonant circuit includes a coil and a marker band. In one embodiment, the resonant circuit is used to induce current in a heater coil element of an embolic coil that passes the resonant circuit to detach the embolic coil.

In one embodiment, a user interface or control system used in an implant delivery system is described. In one embodiment, the interface contains an AC voltage source used to drive a catheter circuit. In one embodiment, the interface is capable of performing a series of steps, such as driving the circuit to find a resonant frequency, sending a resonant frequency to the catheter LC circuit, and/or indicating when a proper implant detachment junction is aligned with the catheter circuit.

In one embodiment, a method of implant delivery is described. The method involves tracking a delivery pusher connected to an implant through a catheter, and then driving a resonant frequency through the delivery catheter to interact with a heater coil detachment junction element of the delivery pusher to deploy an implant at a target region.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Embolic coils are frequently used for occlusive purposes for various therapeutic benefits in different vascular procedures. The embolic coils are placed in a target area to occlude blood flow to the area for a therapeutic benefit. For instance, embolic coils can be placed within an aneurysm to occlude the aneurysm and cut off flow to the aneurysm over time to minimize the risk of aneurysm rupture. Occlusion, as well as embolic coil used for occlusive purposes, is used in a variety of scenarios, including treatment of aneurysms, fistulas, arteriovenous malformations, left atrial appendage, fallopian tube occlusion, vessel shutdown.

Generally, embolic coils are connected to a mechanical pusher and delivered through a delivery catheter to the treatment site in this manner. Some mechanical, electrolytic, or thermal means integral to the delivery pusher are then typically used to detach the coil from the pusher. U.S. Pat. Nos. 8,182,506, 9,414,819, 10,076,338, 9,717,500, 9,867,622 disclose thermal detachment means and are hereby incorporated by reference in their entirety.

It is difficult to develop a detachment system that can consistently and reliably detach; detachment failure can lengthen procedure times and therefore detachment reliability is important. This problem is magnified as the embolic coils are sized down—for instance, when coils are used in the neurovasculature (e.g., to treat brain aneurysms). The embolic coil detachment system must also be sized smaller along with the smaller embolic coils, which can create issues with designing a smaller detachment system that can ensure proper and consistent detachment. Furthermore, the typical embolic coil procedure can require several coils to be placed within the treatment site to sufficiently occlude the target site. The technique of pushing the embolic coil through the catheter to the treatment site, detaching the coil, withdrawing the pusher, and tracking another pusher and coil through the catheter can take considerable time. Additionally, as more coils are used in the procedure, there is a greater risk that the coils can fall out of the target treatment area (e.g. aneurysm) and either jut out of the treatment area and create potential clot risks or leave the treatment area completely and create clot risks at another region of the vasculature. Finally, typical detachment systems typically utilize a proximal voltage source and a set of wires linking the voltage source to the distal pusher-mounted detachment mechanism. The inclusion of these wires can increase the size of the delivery pusher, which can be problematic as the implant and implant delivery system is sized down (e.g., for neurovascular procedures, such as treatment brain aneurysms).

The following embodiments address these issues by utilizing a resonant circuit to detach an implant, including an embolic coil. The concept can be used in a variable detachment embolic coil, where a plurality of detachment regions are located along a single coil whereby a customizable amount of coil can be delivered to target treatment site.

Resonant circuits, also known as LC circuits or tank circuits, utilize an inductor and a capacitor. When driven at their natural frequencies, these circuits create a magnetic field which can then induce a current in a nearby object. When the nearby object is a coiled wire, the current will pass through the coiled wire thereby heating it. This concept can be used to induce heat in a heater coil, where the resonant circuit induces the current to heat the heater coil, and the heater coil when heated severs some connecting element to detach the embolic coil. In typical circuits, especially those used in traditional embolic coil detachment systems, wires are used to ferry current from the proximal end of the pusher (e.g., from a proximal voltage source) to a distal end of the pusher (e.g., to the actual detachment interface, for instance a severable tether); whereby the current is conveyed along the pusher itself. Since the current going into the detachment mechanism/interface generally matches the current coming out of it, larger wires are needed. The inclusion of the wires can increase the size of the delivery pusher which is problematic for smaller implants (e.g., those used in the neurovascular space) where smaller catheters and needed to access smaller blood vessels.

One advantage of a resonant circuit system like the one described is that a relatively small current (which does not require large wires) can be sent to the catheter's resonant circuit and the resonant circuit will in turn induce a current in the pusher-mounted heater coil. Since the resonant circuit is part of the larger catheter rather than the smaller delivery pusher which is tracked through the catheter (meaning the voltage source is connected to the catheter, and the current is ferried along the catheter rather than the pusher), the system can accommodate larger wires to ferry current from a proximal part of the catheter to a distal part of the catheter since the pusher is not needed to transmit current. When the catheter-mounted resonant circuit is driven at its natural frequency, it will induce a large current in the pusher-mounted heater, thereby heating the heater and detaching the implant.

Figure 1:
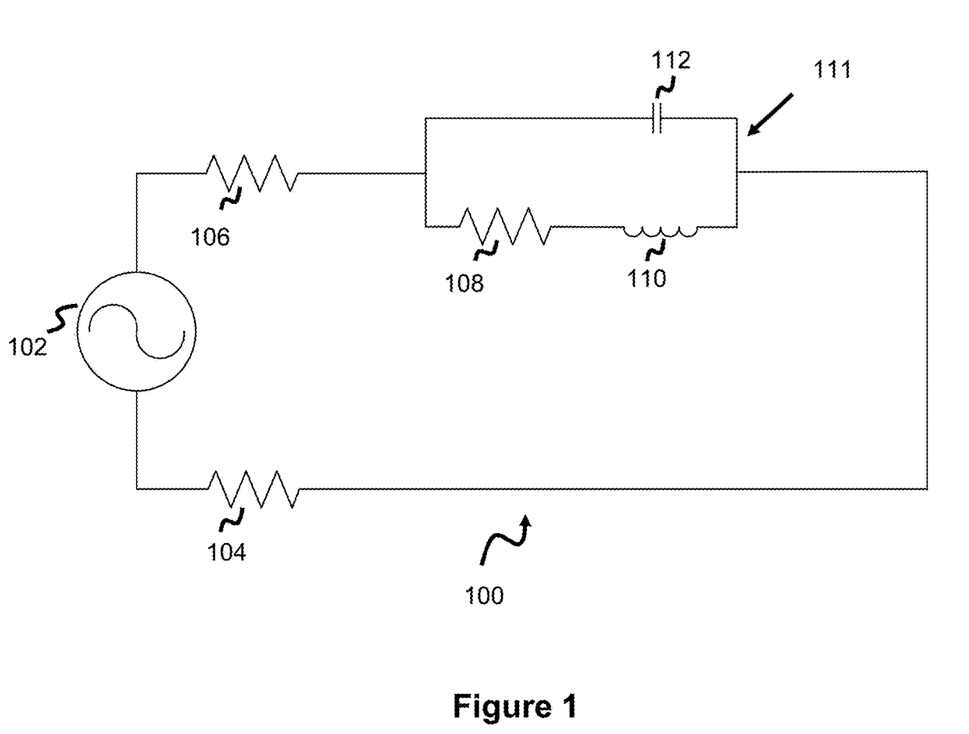
FIG. 1 illustrates a circuit diagram for a resonant circuit used in an implant detachment system, according to one embodiment.

FIG. 1 shows a schematic diagram of a circuit 100 which includes the resonant circuit concept as it is used in an embolic coil detachment system. Circuit 100 includes a resonant circuit 111, which in turn includes a capacitor 112 which takes the form of a pair of marker bands with a gap in between (which will be discussed later) and an inductive coil 110. The inductor coil 110 has a particular resistance 108 which is accounted for in the resonant circuit. A proximal AC voltage source 102 provides the voltage to drive the circuit, and lead wires 104, 106 connect to the resonant circuit 111 and have a particular resistance associated with the wires as indicated in FIG. 1. The proximal AC voltage source would drive the circuit at the particular natural frequency of the resonant circuit so that the circuit can then induce a current in a nearby object. The proximal AC voltage source would be integrated in a proximal control mechanism, such as a handheld detachment system connected to the catheter or a detachment system mounted to the proximal portion of the catheter with all the integrated controls and circuitry. Circuit 100 is all catheter mounted, meaning the AC voltage source 102 is connected to the delivery catheter, wires 104 and 106 span the length of the delivery catheter ferrying current from the voltage source to the LC circuit comprising capacitor 112 and inductor coil 110 which are located at a distal portion of the catheter.

The system would either already have the catheter's resonant frequency pre-programmed, or alternatively would be able to deduce the resonant frequency so that the circuit is driven at its resonant frequency. In one example utilizing the former approach, the resonant frequency would be calculated when the device is assembled based on the capacitance and inductance values and this resonant frequency is then programmed into the system. In one example utilizing the latter approach, AC voltage source 102 would have the means to deduce the resonant frequency based on the characteristics of the resonant circuit and then drive the circuit at this particular resonant frequency. The resonant frequency is calculated by taking the inverse of the square root of the inductance of the inductor coil 110 multiplied by the capacitance of capacitor 112, expressed in radians as $1/\sqrt{LC}$, or in hertz as $1/2\pi\sqrt{LC}$. The control mechanism could test the circuit with various frequencies to test which frequency corresponds to the resonant frequency, or alternatively the control mechanism could implicitly test for the inductor and capacitance values and then calculate the resonant frequency in this way. The voltage source 102 could be incorporated into a larger handheld unit or user-interface, which would contain the voltage source as well as any computational interface needed to determine the resonant frequency.

Figure 2:
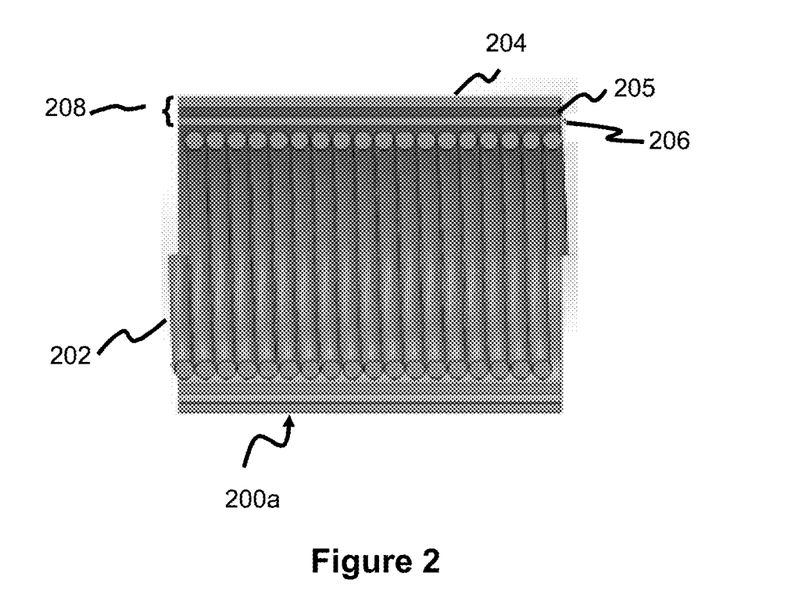
FIGS. 2-4 illustrates a tubular band and coil configuration used in an implant detachment system, according to various embodiments.

The resonant circuit would be utilized at the distal portion or the distal end of a catheter, where the embolic coil is delivered through the catheter by a mechanical pusher which is tracked through the catheter. Referencing FIG. 1, the distal portion of the catheter would therefore include capacitor 112 and inductor 110, while wires 104 and 106 span the length of the catheter delivering current from the voltage source 102 to the distal resonant circuit 111. The capacitor, as discussed above, is formed from a pair of marker bands with a gap in between, thereby taking the configuration of a parallel-plate capacitor. This is best shown in FIG. 2 where there are two tubular elements forming the capacitor; an inner tubular element 206, an outer tubular element 204, and a gap 205 which functions as the dielectric—all these elements form capacitor 208. In one example, a polymer insulator fills this gap 205 and functions as the dielectric while in another example there is just air in the gap 205 which functions as the dielectric. In one example, tubular elements 204 and 206 are comprised of radiopaque material (e.g., comprised of tantalum, platinum, copper, tungsten, silver, gold, and/or palladium) and take on the form of radiopaque marker bands, to thereby enable visualization of the distal section of the catheter. In other embodiments, non-radiopaque metallic material (e.g., nitinol, stainless steel, aluminum, cobalt-chromium, or other materials) are used to form the capacitor 208. Note, for the purposes of the Figures it appears there is a top capacitor (the set of parallel plates at the top of the catheter) and a bottom capacitor (the set of parallel plates at the bottom of the catheter); however, since the marker bands are tubular and since this is a side cross-sectional view, the marker band elements extend circularly around the catheter and therefore there is no "top" and "bottom" capacitor—instead these are elements of the same common tubular capacitor just placed in a tubular fashion around the catheter, comprising an inner tubular element 206, an outer tubular element 204, and a gap 205 in between.

Figure 3:
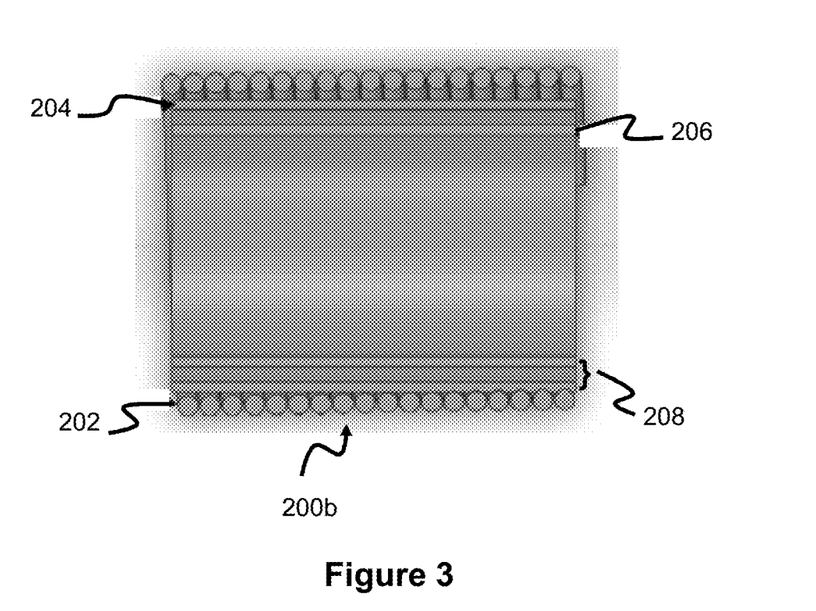

The inductor is formed of a metallic coil 202. Metallic inductor coil 202 can be comprised of radiopaque substances such as platinum, copper, tungsten, or silver or non-radiopaque substances such as nitinol or stainless steel. The inductor 202 can occupy three positions relative to the capacitor 208, as shown in FIGS. 2-4; meaning the inductor 202 can either sit radially inside the capacitor 208, radially outside the capacitor 208, or between the tubular elements forming the capacitor 208.

As shown in FIG. 2, the inducting coil 202 is part of the catheter assembly but placed within the inner tubular element/inner marker band 206. The inductor coil is not in direct contact with the inner marker band 206, however a solder joint can be used at either end of the coil to create a conductive region between inductor coil 202 and capacitor 208. An insulative material, such as a polymeric sleeve or polymeric layer can also be placed between the inductor coil 202 and capacitor 208 (specifically, inner marker band 206) to limit the current flow between inductor coil 202 and capacitor 208 to just the solder joint locations. In some examples, a portion of the windings of the inductor 202 can also be coated with insulative material to limit conductivity outside of the coil itself. For the purposes of the configuration shown in FIG. 2, a first wire is soldered to inner marker band 206, a second wire is soldered to outer marker band 204, and inductive coil 202 is soldered to inner marker band 206 at a particular location. The first and second wires (represented as resistive elements 104 and 106 in FIG. 1) are connected to the AC voltage source, and in this way the circuit (schematically shown in FIG. 1) is created. The first and second wires 104 and 106 will also have their own resistance, as noted in the circuit model of FIG. 1. Alternatively, a first wire connects to the inductive coil 202, a second wire connects to either inner marker band 206 or outer marker band 204 and the inductive coil 202 is soldered in a particular location to inner marker band 206 to provide an electrical path between the capacitor 208 and inductor 202.

In FIG. 2, the inductive coil 202 is placed within radially inner marker band 206. FIGS. 3-4 show alternative configurations of how the inductive coil 202 could be positioned relative to the marker-band capacitor 208. In the configuration shown in FIG. 3, inductive coil 202 is placed radially outside of outer marker band 204. A solder joint is used to establish electrical connection between inductive coil 202 and capacitor 208 (wherein capacitor 208 is composed of inner and outer marker bands 204, 206 as described earlier). A first wire connects to the inductor coil 202 while a second wire connects to either the inner marker band 206 or the outer marker band 204, where the two wires proximally connect to the AC voltage source. There is insulative material placed between the inductor coil 202 and capacitor 208 in order to limit electrical communication between the two elements solely to the location of the solder joint. In one example, a polymer layer can be placed between inductor coil 202 and outer marker band 204 to act as an insulator. The inductor coil 202 itself, in one example, can also include an insulative material around the coil windings to limit current outflow outside of the coil.

Figure 4:
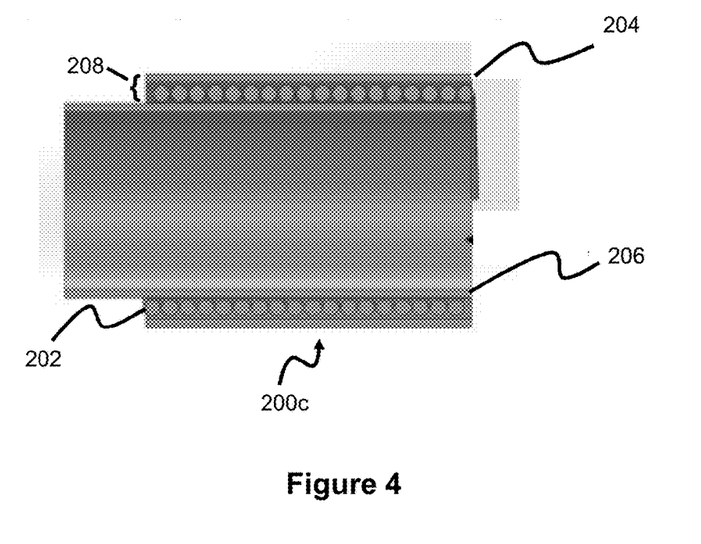

In FIG. 4, inductor coil 202 is placed within the capacitor 208 structure, such that the inductor coil 202 is placed between the inner and outer marker bands 206, 204. One advantage to this design is creating a smaller catheter profile since no additional space is needed for the coil since its placed between the marker bands. However, one major issue is being able to electrically isolate the inductor coil 202 from the capacitor 208 structure since the inductor coil is actually placed physically within the capacitor structure. An insulative material can be placed on the inner marker-band facing and outer marker-band facing sides of the inductor coil 202 structure to help insulate the inductor 202 from the capacitor 208. This insulative layer should comprise all of the open space that exists between the marker bands 206 and 204, so basically the space between the marker bands comprises only the inductor coil 202 and the insulative layer/material. In one example, the inductor coil 202 itself can utilize additional polymeric insulative material between a portion of the coil windings to limit current discharge away from the coil. Various wire connection configurations are possible to connect the system to an AC voltage source. In one example, a first wire connects to the inner marker band 206, a second wire connects to the outer marker band 204, and a solder junction is utilized between the inductor coil 202 and one of the two marker bands to establish communication between the inductor and the capacitor 208. In another example, a first wire connects to the inductor coil 202, a second wire connects to one of the inner or outer marker bands 206 or 204, and a solder junction is used between the inductor coil 202 and one of the two marker bands.

The description thus far has focused on the catheter structure which utilizes a resonant/tank/LC circuit integral to the catheter itself. The catheter itself utilizes a capacitor 208 (comprised of inner and outer tubular bands 206, 204) and an inductor coil 202 to create the LC circuit. The inductor coil 202 and capacitor 208 (composed of inner and outer tubular bands 206, 204) can be built into the catheter in a number of ways. In one example, the distal section of the catheter can include these structures in the walls of the catheter, such that the inductor coil 202 and inner and outer tubular bands 206, 204 are placed within the catheter wall. In another example, the inductor coil 202 and outer tubular bands 206, 204 are built over the outer wall of the catheter. In another example, the inductor coil 202 and outer tubular bands 206, 204 are built "under" the catheter wall such that they radially project from the inner lumen of the catheter. In another example, this structure is attached to the distal end of the catheter where the inner and outer tubular bands 206, 204 and the inductor coil 202 is physically attached to the distal end of the catheter to create the circuit while keeping the continuous lumen throughout the length of the catheter. The wires which ferry current between the proximal AC voltage source and the distal LC circuit can track through the wall of the catheter, can be placed within the catheter lumen, can be placed over the catheter or spiral around the catheter, or can be part of a reinforcing coiled or braided element spanning the length of the catheter.

The catheter LC circuit is driven at its natural frequency whereby an impulse corresponding to the circuit's natural frequency is sent from the voltage source to the resonant circuit. This creates a magnetic field that can induce a current in a nearby coil. This, in turn, induces a current in part of the delivery pusher being delivered through the catheter in order to detach an implant coupled to the delivery pusher, in a manner that will now be described.

Figure 5:
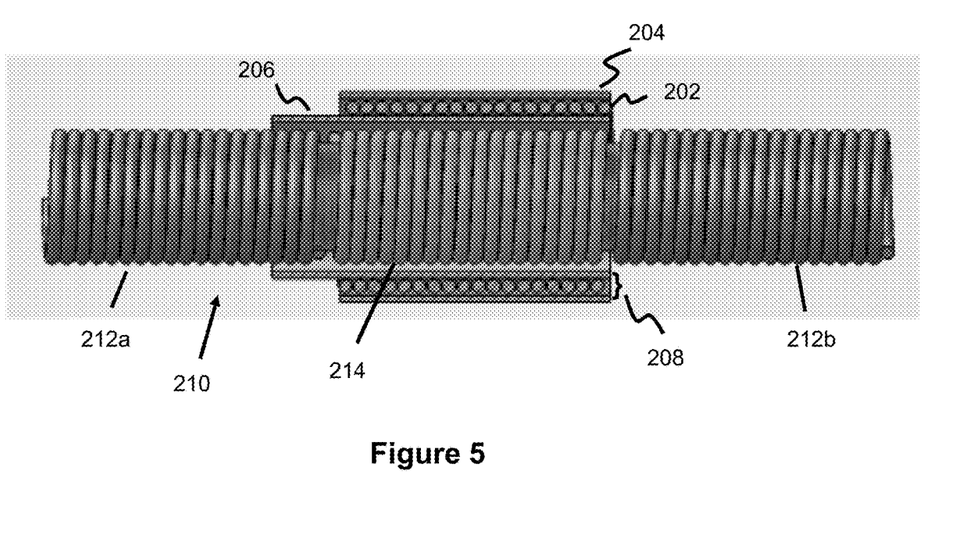
FIG. 5 illustrates a detachment segment of an embolic coil passing through a resonant circuit-based embolic coil detachment system, according to one embodiment.

FIG. 5 shows how the embolic coil detachment system would be used in operation to detach embolic coil from the pusher. A distal section of the catheter includes the LC circuit—comprising a capacitor made from inner marker band 206 and outer marker band 204, and an inductive coil 202. The particular detachment system shown utilizes the configuration shown in FIG. 4, where the inductor coil 202 is placed between the marker bands of the capacitor, however any of the embodiments shown in FIGS. 2-4 can be used meaning the inductor coil 202 can be placed in various places relative to the tubular elements/marker bands of the capacitor.

Figure 6:
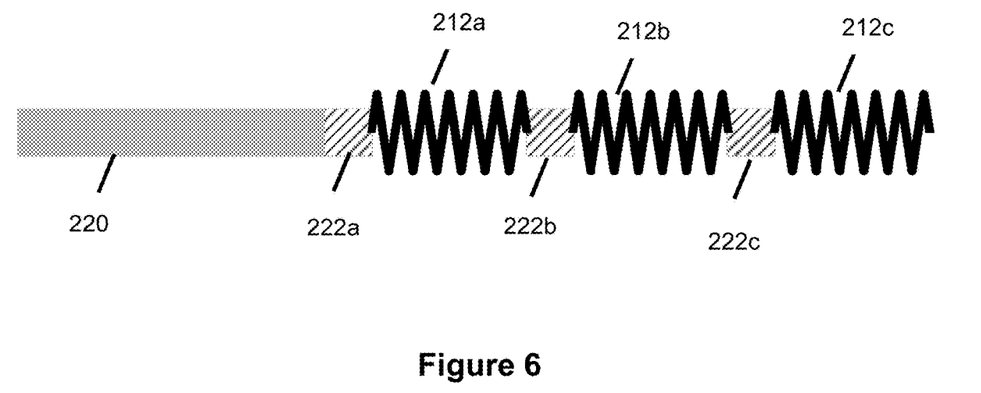
FIG. 6 illustrates a pusher and embolic coil with a plurality of detachment junctions, according to one embodiment.

Embolic coil 210 is delivered through the catheter and through the distal section of the catheter which utilizes the LC circuit, including the inductor coil 202 and the capacitor 208 formed of inner marker band 206 and outer marker band 204. Embolic coil 210 includes a plurality (e.g. 2 or more) embolic coil segments 212a, 212b separated by a detachment segment 214—this would form a variable detachment coil where various coil segments have detachment segments in between. The detachment segment functions as a detachment point such that a customized amount of the embolic coil is deposited in the vasculature, where the user could determine how much embolic coil is needed and then initiate detachment at a particular detachment segment to detach and deploy a metered amount of embolic coil. This arrangement-type is further shown in FIG. 6 where a pusher 220 is used to push a number of embolic coil segments 212a, 212b, 212c each separated by detachment junctions 222a, 22b, 222c which are placed between the various embolic coil segments.

Figure 7:
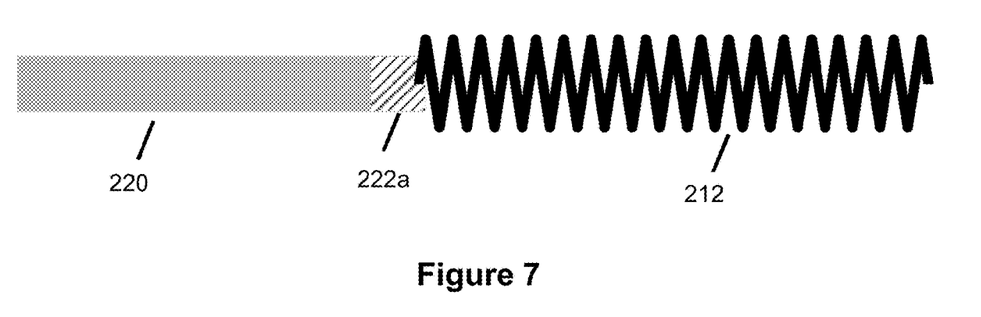
FIG. 7 illustrates a pusher and embolic coil with one detachment junction, according to one embodiment.

An alternative embodiment of the embolic coil would still utilize detachment segment 214, but one continuous embolic coil segment sits distal to the detachment segment 214 and a pusher (not shown in FIG. 5, but shown in FIG. 7) is proximal to the detachment segment 214. In this embodiment, detachment segment 214 would represent the one and only dedicated detachment point to detach embolic coil from the pusher. In this way, a user would use the LC circuit to detach a set amount of coil, and then track more embolic coil through the catheter if more embolic coils were required for occlusion. One advantage of this setup compared to the conventional approach is that since the LC circuit is part of the catheter, all the current ferrying wires are utilized on the catheter rather than on the embolic coil pusher, meaning the embolic coil pusher can be sized smaller and therefore smaller embolic coils can potentially be used compared to what otherwise would be feasible. This configuration is shown in FIG. 7, where pusher 220 is used to push one contiguous embolic coil segment 212 with one detachment junction 222a.

Figure 8:
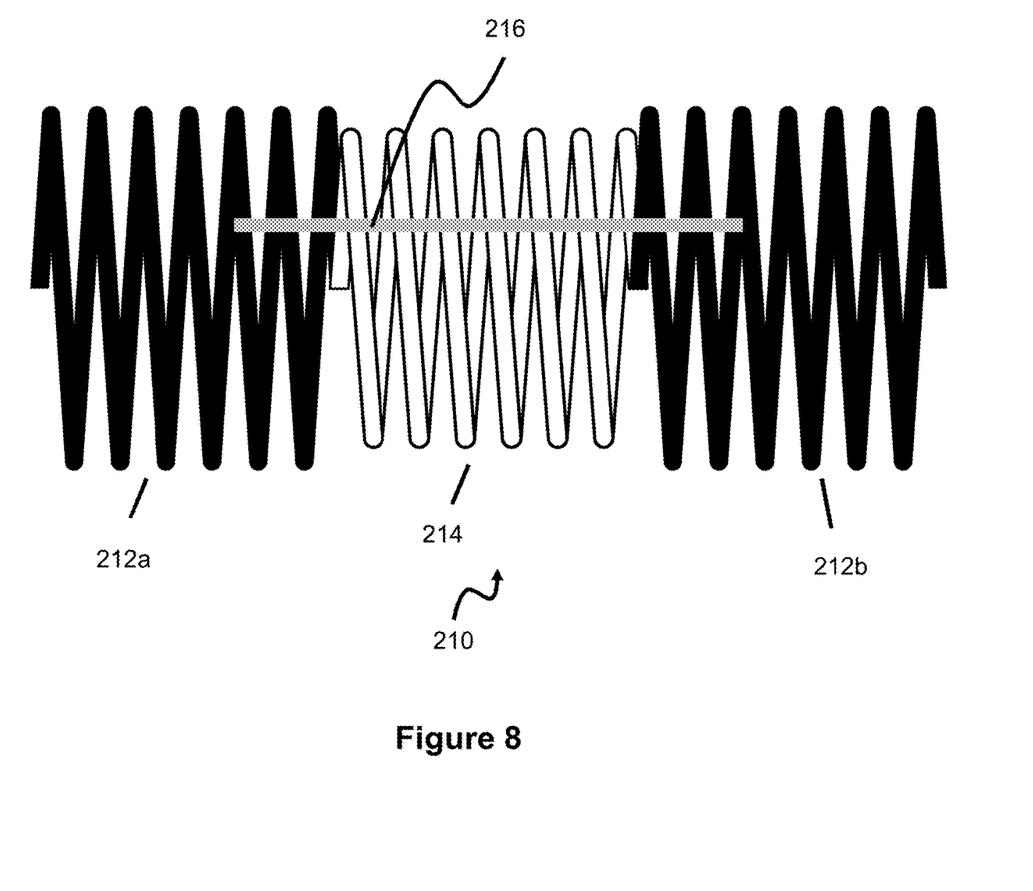
FIG. 8 illustrates an embolic coil including an embolic coil segment and a detachment segment, according to one embodiment.

The embolic coil 210 includes the detachment segment 214 as shown in FIG. 5. In one embodiment, the detachment segment 214 takes the form of a heater coil comprised of a metallic (e.g., nitinol, platinum, tungsten, copper, silver) coil; heat is generated as current passes through the adjacent windings of the coil. A tether spans the heater coil, the tether is connected at one end to distal embolic coil segment 212a and at the other end to proximal embolic coil segment 212b, as shown in FIG. 8. The tether can be made of a number of materials, for instance polymers such as PTFE, PTE or Engage, or metallic wire. Heat generated in the heater coil segment severs this tether, detaching both the distal coil segment 212a and the heater coil segment 214. A metallic wire is connected to the two ends of the heater coil to prevent shorting. Please note, in the embolic coil embodiments where one single heater coil segment is used to detach the embolic coil from the pusher, the heater coil design is the same and severing the tether will cause the embolic coil to detach from the pusher. The heater coil detachment segment causes tether 216 to degrade or melt as the heater coil heats up, thereby detaching the distal embolic coil segment 212a from the rest of the embolic coil 210. In various embodiments, the detachment segment 214 can either detach along with distal coil segment 212a or can remain with proximal segment 212b, this is just based on how the detachment segment 214 is connected to the other embolic coil segments.

As discussed above, when the catheter's LC circuit is driven at its resonant frequency it will create a magnetic field which will, in turn, induce a current in the pusher's heater coil when the heater coil is aligned with the LC circuit. The proximal control system which includes the AC power source will drive the circuit at this resonance frequency. When the heater coil segment is aligned with the LC circuit, current will flow through the heater coil, generating heat which will eventually degrade and detach the tether.

The AC power source is part of a control system or user interface which is connected to the catheter itself, therefore the proximal end of the catheter can include or can be connected to the AC power source. The control system would include circuitry and an integrated system which could, in some embodiments as described earlier, calculate the resonant frequency or drive the circuit at various frequencies to derive the resonant frequency. The embolic coil/implant is a separate structure entirely since it is delivered through the catheter via the pusher; the embolic coil/implant can be thought of as a passive implant device which electrically communicates with a "smart" catheter to initiate detachment of the implant from the pusher.

In one embodiment, the control system utilizes appropriate circuitry to tell when the heater coil segment of the embolic coil passes the resonant circuit of the catheter. In one example, a resistance measurement system could be used based on the heater coil material where a certain resistance would register in the circuit as the heater coil passed the resonant circuit, this could be especially useful since the heater coil material would differ from the embolic coil material and therefore a different resistance would register. In another example a magnetic detection circuit could be used where the heater coil would exert a slight magnetic pull on a portion of the catheter (either the resonant circuit, or a separate circuit system embedded in the catheter) which would indicate that the heater coil is properly aligned with the resonant circuit. At this point a prompt, such as an audible sound or a light (e.g. a green light) on the proximal AC power source control system would be generated, thereby indicating that the embolic coil is in a detachment position where the heater coil is aligned with the resonant circuit. The user would then take some action (e.g. press a button) to send the resonant frequency through the catheter circuit to heat the embolic coil's heater coil thereby detaching the embolic coil.

Note the detection function described above, which detects when the pusher's detachment junction heater coil is properly aligned with the catheter's LC circuit, can be done with or without physical contact. In one embodiment which does not utilize physical contact to sense the appropriate detachment point, the described magnetic detection circuit or resistance measurement can be done without the heater coil of the implant delivery pusher physically contacting the catheter, and is based on the pusher's heater coil exerting a certain magnetic pull or resistance as the heater coil passes in close proximity to the catheter's LC circuit but without physically touching the catheter at all. In another embodiment which utilizes physical contact to sense the appropriate detachment point, the interior surface of the catheter at the LC circuit interface (in other words, the portion of the catheter containing the inductor coil and capacitor) can have one or more inwardly extending fingers or projections, and these extending fingers/projections would "read" the pusher segment to determine either a resistance or a certain magnetic pull. When the heater coil detachment junction of the delivery pusher passes through this region, the proper resistance or magnetic pull is measured, and the audible or visual signal is given to the user indicating that a proper detachment junction region is identified. Alternative embodiments can disregard the detection system entirely and instead the user would determine when a sufficient amount of embolic coil is deployed through imaging, then would initiate a detachment command (e.g., by pressing a button on the user interface), the system would then store this command and then identify when the detachment junction is next aligned with the LC circuit and initiate the detachment by driving the LC circuit with the proper resonant frequency to initiate detachment.

The catheter used to create the LC circuit can be thought of as a powered catheter since rather than the traditional catheters which just passively act as a conduit, here the catheter includes circuitry components (e.g., the inductive coil and capacitor) to create a circuit to interface with elements that pass through the catheter. Whereas typical implant delivery systems utilize a wired implant pusher to detach the implant through a passive catheter, here the approach generally involves utilizing a "smart" catheter which interfaces with a passive implant which contains one or more detachment points.

Please note, although the description mostly discusses the resonant/LC/tank circuit system being used as part of an implant detachment system utilizing embolic coils, the resonant/LC/tank circuit can be used with a variety of medical implants aside from embolic coils such as stents, occlusive coils, occlusive plugs, etc. The system described can be used with a variety of implants since all that is needed is a pusher with a detachment junction as described. The system described offers some benefit with a variable detachment embolic coil system since the system can utilize a plurality of detachment points and the user can detach a customized segment of the embolic coil within a target treatment site.

The embodiments described herein primarily discussed a heater coil detachment junction mechanism. Please note, various other detachment junction mechanisms are also possible, as the principles discussed utilize an LC circuit inducing a current in a nearby object, where this induced current is then used to activate a part of the detachment junction to sever an implant from the detachment junction. U.S. Pat. No. 9,808,599B2, which is hereby incorporated by reference in its entirety, discloses various detachment junction concepts used in a variable detachment embolic coil where a plurality of coil segments are separated by detachment junctions. These alternative detachment junctions could also be used along with the principles espoused here, wherein a catheter-mounted LC circuit induces a current in the implant detachment junction to sever and release the implant.

What is claimed is:

1. An implant delivery system comprising:
   a voltage source;
   a catheter;
   an LC circuit located on the catheter and connected to the voltage source, the LC circuit having a capacitor and an inductive coil;
   a pusher distally connected to an implant, the implant and pusher configured to be delivered through the catheter;
   a detachment junction between the pusher and the implant;
   the voltage source operable to provide current through the LC circuit so as to induce a current through the detachment junction of the pusher sufficient to detach the implant from the pusher.

2. The implant delivery system of claim 1, wherein the capacitor comprises an inner tubular marker band and an outer tubular marker band.

3. The implant delivery system of claim 2, wherein the inductive coil is placed under the inner tubular marker band, over the outer tubular marker band, or in between the inner tubular marker band and the outer tubular marker band.

4. The implant delivery system of claim 1, wherein the voltage source is part of a user interface.

5. The implant delivery system of claim 4, wherein the user interface can calculate a resonant frequency of the LC circuit.

6. The implant delivery system of claim 5, wherein the user interface is capable of driving the LC circuit at its resonant frequency.

7. The implant delivery system of claim 1, wherein the voltage source is an AC voltage source.

8. The implant delivery system of claim 1, further comprising one or more wires spanning the catheter and linking the voltage source to the LC circuit.

9. The implant delivery system of claim 1, wherein the current flowing through the LC circuit of the catheter induces the current through the detachment junction of the pusher without the pusher and the catheter physically touching.

10. The implant delivery system of claim 1, wherein the implant is an embolic coil.

11. An implant delivery system comprising:
    a voltage source;
    a catheter having a distally located LC circuit constituted by an inner tubular element, outer tubular element, and a coil;
    a pusher distally connected to an implant, the implant and pusher configured to be delivered through the catheter;
    a detachment junction between the pusher and the implant;
    the voltage source operable to provide current through the LC circuit so as to induce a current through the detachment junction of the pusher to detach the implant from the pusher.

12. The implant delivery system of claim 11, wherein the detachment junction includes a heater coil and a tether spanning the length of the heater coil.

13. The implant delivery system of claim 12, wherein the current flowing through the LC circuit of the catheter induces current to flow through the heater coil, thereby severing the tether and detaching the implant from the pusher.

14. The implant delivery system of claim 11, wherein the implant is an embolic coil.

15. The implant delivery system of claim 14, wherein the embolic coil includes a plurality of embolic coil segments.

16. The implant delivery system of claim 15, further comprising a plurality of detachment junctions where a detachment junction is placed between each set of the embolic coil segments.

17. The implant delivery system of claim 11, wherein the catheter's inner tubular element and outer tubular element comprise a capacitor, and the catheter's coil comprises an inductor coil.

* * * * *